United States Patent [19]
Karger et al.

[11] Patent Number: 5,571,398
[45] Date of Patent: Nov. 5, 1996

[54] PRECISE CAPILLARY ELECTROPHORETIC INTERFACE FOR SAMPLE COLLECTION OR ANALYSIS

[75] Inventors: Barry L. Karger, Newton; Frantisek Foret, Malden; Odilo Muller, Chestnut Hill, all of Mass.

[73] Assignee: Northeastern University, Boston, Mass.

[21] Appl. No.: 363,474

[22] Filed: Dec. 23, 1994

[51] Int. Cl.$^6$ .................................................. C25B 9/00
[52] U.S. Cl. .......................................... 204/603; 204/601
[58] Field of Search ........................... 204/299 R, 180.1, 204/182.8

[56] References Cited

U.S. PATENT DOCUMENTS

| | | | |
|---|---|---|---|
| 4,842,701 | 6/1989 | Smith et al. | 204/180.1 |
| 4,911,807 | 3/1990 | Burd | 204/180.1 |
| 5,126,025 | 6/1992 | Carson et al. | 204/180.1 |
| 5,149,661 | 9/1992 | Gjerde et al. | 436/178 |
| 5,169,510 | 12/1992 | Lunte et al. | 204/229 R |
| 5,169,511 | 12/1992 | Allington et al. | 204/299 R |
| 5,202,010 | 4/1993 | Guzman | 204/299 R |

OTHER PUBLICATIONS

Roach et al., "Determination of Methotrexate and Its Major Metabolite, 7-Hydroxymethotrexate, Using Capillary Zone Electrophoresis and Laser-Induced Fluorescence Detection", J. of Chromatography, 426 (1988) (no month), pp. 129–140.

Smith et al. "Improved Electrospray Ionization Interface for Capillary Zone Electrophoresis–Mass Spectrometry", Anal. Chem., 60(18), Sep. 15, 1988, pp. 1948–1952.

Goodlett et al., "Reduced Elution Speed Detection for Capillary Electrophoresis/Mass Spectrometry", J. Microcol. Sep. 5:57–62 (1993) (no month).

Primary Examiner—Kathryn Gorgos
Assistant Examiner—Edna Wong
Attorney, Agent, or Firm—Weingarten, Schurgin, Gagnebin & Hayes

[57] ABSTRACT

A capillary electrophoretic system and method for accurate and precise post-column manipulation of molecules separated by capillary electrophoresis is disclosed. The system of the invention includes a separation capillary; a detector positioned close to, and preferably less than approximately one cm from the outlet end of the capillary; and a sheath which surrounds and directs a collection buffer over the capillary outlet end. With the detector positioned as described, precise and accurate correlation is possible between detection of the separated components of a sample and their emergence from the capillary. The detector preferably includes optical fibers connected to a spectrophotometric detection method, such as UV detection or fluorescence, including laser induced fluorescence. The sheath collection buffer, the capillary and an electrophoresis buffer reservoir, for supplying buffer to the inlet end of the capillary, are in electrical contact in an electrical circuit and provide the electric field required for separation of a sample of molecules. The separated components of the sample are mixed with collection buffer as they emerge from the outlet end of the capillary. They are then collected into or on any collection device, such as vials, collection capillaries or membranes, or they are transferred to other devices for further analysis, such as mass spectroscopy.

39 Claims, 5 Drawing Sheets

PRECISE CAPILLARY ELECTROPHORETIC INTERFACE FOR SAMPLE COLLECTION OR ANALYSIS

FIELD OF THE INVENTION

The invention relates to capillary electrophoresis, and more particularly to collecting and/or analyzing sample components exiting from a capillary electrophoretic separation system.

BACKGROUND OF THE INVENTION

Capillary electrophoresis (CE) has proven to be a powerful technique for analysis of complex mixtures of biological molecules, offering advantages not available with conventional separation methods, such as HPLC or column chromatography. One advantage of CE is the speed of the analysis. Frequently, a sample can be analyzed by CE in a span of time on the order of minutes, whereas conventional techniques often require several hours or more. The low volume of sample required is another advantage of this technique. Samples of only a few nanoliters are easily analyzed by CE; other separation techniques usually require samples of more than one $\mu$l. The low CE sample size requirement allows the remainder of the sample volume to be used for other manipulations or further analyses. An additional advantage is the possibility for high resolution of the sample into its component parts with component molecules separated by CE eluting in very narrow bands. This capability allows the user to analyze a sample of very similar molecules, e.g., DNA fragments with a single base change or proteins with a single amino acid substitution.

Although the advantages of capillary electrophoresis allow an investigator to process a very small sample, current methods of collecting or removing the separated components are limited by the small volumes (approximately a few nL) of fractionated materials that elute from the capillary tube and the imprecise way the samples are usually collected. Available sample collection devices for use in CE generally use electroelution (including the movement of ions with or without electroosmotic flow) or pressurized flow.

Electroelution methods of sample collection employ standard capillary electrophoretic equipment. The user must know several variables of the system including the velocity of migration of a selected sample, and the distance between the on column detection point and the end of the capillary. After detection of a zone of interest, the time required for the zone to traverse the distance between the detection point and the capillary exit is calculated. In one general system, the electric current is then turned off, and the CE capillary is removed from the CE apparatus and placed into a collection vial containing a collection buffer and a platinum electrode. To collect the zone, current is applied for a predetermined time so that the zone migrates from the capillary into the collection vial. In some cases, pressure can be applied to remove the sample from the capillary. After collection of the zone, the capillary is moved back to the electrode reservoir and the analysis can continue. Alternatively, a collection capillary containing a collection buffer and electrode can be positioned adjacent to the exit end of the capillary while the electric current is off. The current is then resumed for collection of the zone of interest.

Electroosmotic elution can be used in cases when electroosmotic flow is present in the electrophoretic system. The end of the capillary used in this approach has a microscopic fracture located after the detection point. The microscopic fracture is immersed in the electrode buffer reservoir to provide the electric contact for completion of the circuit. As electroosmotic flow transports the liquid inside the CE capillary, the separated zones move past the fracture and most of the material can be collected in appropriate vials once the time of their appearance at the capillary exit is calculated.

Capturing segregated samples on membranes represents another approach for collecting samples from a capillary electrophoretic separation. In this approach, the exit end of the capillary is in contact with a wetted surface of a moving membrane (e.g., cellulose acetate, polyvinylidene difluoride (PVDF), or nitrocellulose) which is connected to the electrode. As the separated zones elute from the capillary, they are deposited on the surface of the membrane. The collected fractions are not obtained in a solution form, and their location on the support can be difficult without further sample treatment (blotting, staining).

It is also known to combine CE directly with other detection systems, e.g., mass spectroscopy. In one such system, the sample components emerging from the outlet end of the capillary enter an electrospray ionization (ESI) interface. Sample ions in the gas phase are then transferred to a mass spectrometer for analysis. To increase resident dwell time in the mass spectrometer, step changes can be introduced in the electric field strength of the CE system. For example, prior to elution of the first sample component from the capillary under constant field strength conditions, the electrophoretic voltage can be decreased. This reduction of migration velocity of the emerging components permits more efficient ionization at the ESI interface and an increased number of mass spectroscopy scans can be recorded without a significant loss in ion intensity.

Additional methods of processing the separated components of a sample following CE would be desirable to take full advantage of the high resolution capability of this separation technique. The capillary electrophoretic system and method of the invention provide for an improved interface between a separation capillary and subsequent systems of sample collection or analysis.

SUMMARY OF THE INVENTION

The invention is directed to a capillary electrophoretic system and method for precise and accurate post-column-manipulation of molecules separated by capillary electrophoresis and for collecting or analyzing small volumes of sample components exiting from the capillary system without disrupting the electric current required for separation. The system of the invention includes a separation capillary, which may or may not contain a sieving or interaction matrix, an electrophoresis buffer reservoir to supply electrophoresis buffer to the inlet end of the capillary, a detector positioned close to and preferably less than one cm from the outlet end of the capillary, and a sheath surrounding the outlet end of the capillary to direct a collection buffer for transporting the separated components of an applied sample to collection vessels or to other systems for further analysis. The collection buffer in the sheath is in electrical contact with the capillary and the electrophoresis buffer reservoir in an electric circuit, which provides the electric field required for separation of the component molecules of an applied sample.

The positioning of the detector close to (i.e., a few cm from) and preferably at less than approximately one cm from the outlet end of the capillary is critical and provides for accurate and precise correlation between detection of the components and their emergence from the capillary. The detector can include optical fibers connected to a device for spectrophotometric detection, such as UV detection or fluorescence. At a distance of less than one cm, uncertainty in the elution time of a specific separated component from the sample is reduced to approximately a few seconds. This reduction in error over the prior art enables, precise collection of any DNA fragment separated by CE. Preferably, the detector and any subsequent apparatus are under computer control to achieve exact correlation between sample detection and sample collection or analysis.

It is to be understood that the separation capillary can be a standard circular fused silica capillary or a capillary of any desired shape, such as rectangular, and can be made from any suitable material, e.g., glass, fused silica, or plastic. The separation capillary can also be formed as a groove or a channel micromachined on a planar surface or molded in a block of a suitable polymer such as Plexiglas or polycarbonate. Electrophoretic separation can be carried out with or without the use of a sieving or interaction matrix as desired and in combination with any other appropriate technique, such as isoelectric focusing. In addition, separation can take place in an open tube as capillary zone electrophoresis (CZE), with or without the use of electroosmotic flow.

Post-column processing of sample components exiting a separation capillary in the system of the invention can include any type of collection, isolation, purification or analysis. For example, the collection buffer may be used to transport the separated sample components to analytical devices such as a mass spectrometer or to a collection vessel such as a capillary, vial or membrane. In addition, collected samples may be purified or processed by electrochemical or radioactive analysis or such samples may be derivatized before analysis.

In some cases, excess salt in the sample as applied might cause initial variation in component migration velocities. Therefore, it is also contemplated in the system of the invention to include a secondary detection system between the inlet end of the capillary and the detector previously described to provide more accurate determination of migration velocity.

The system of the invention can include computer feedback control from the detector to regulate the electric field strength of the electrophoresis system. Thus, the sample migration velocity can be slowed or even stopped as desired to permit, e.g., a longer resident dwell time of an emerging sample component in a mass spectrometer such as an ion trap.

DESCRIPTION OF THE DRAWINGS

The invention will be more fully understood from the following detailed description taken in conjunction with the accompanying drawings in which.

DETAILED DESCRIPTION OF THE INVENTION

While high separation efficiency and resolving power make capillary electrophoresis an attractive nanopreparative technique for isolating and collecting small amounts of pure substances, conventional methods of collecting the materials eluting from the capillary column have not permitted full advantage to be taken of this potential. To collect fractions in appropriate vials, capillaries, etc., during CE separation, one must know the exact time when a zone appears at the exit end of the capillary. This time can be calculated by using the migration rate of the zone from the injection end to the detection point, and length between the detection point and the exit end of the capillary. However, the variation of migration rates in capillary electrophoresis can be on the order of 2% or more. Thus, the longer the distance between the detection point and the exit end of the capillary, the larger the absolute variations in the elution times. For example, if the distance between the detection point and the exit end of the capillary is 10 cm (with a typical migration time of 1000 sec for DNA fragments), the variation of the migration times would be approximately ±20 seconds. While this uncertainty is not critical for low resolution separations, it is not acceptable in the case of separation and collection of DNA fragments by CE where the entire resolved zone width is approximately 10 seconds or less and the spacing between consecutive zones may be an even shorter length of time. Thus, the zones produced on a capillary electrophoretic separation require precise and accurate correlation between detection and collection. In theory, if the distance between the detection point and the exit end of the capillary were reduced, the absolute uncertainty in the elution time could be reduced proportionally. However, to date such an improvement has not been made due primarily to the bulky detectors available for CE work and the electrical requirements of the CE system.

Conventional CE systems use a standard UV detector including a light source and a photosensing element enclosed in a large housing. The large dimensions of the detector generally restrict the placement of the detection point to no less than approximately 10 cm from the exit end of the capillary. In addition, the CE unit requires a closed electric circuit. Electric current flowing through the capillary forces the ions of the sample to be separated according to their migration velocities as they proceed through the buffer. The equipment needed to provide the electric current includes electrodes and buffer reservoirs located at each end of the capillary. These components take up much space and have generally also restricted the minimum collection volume to 10 µl or more.

Figure 1:
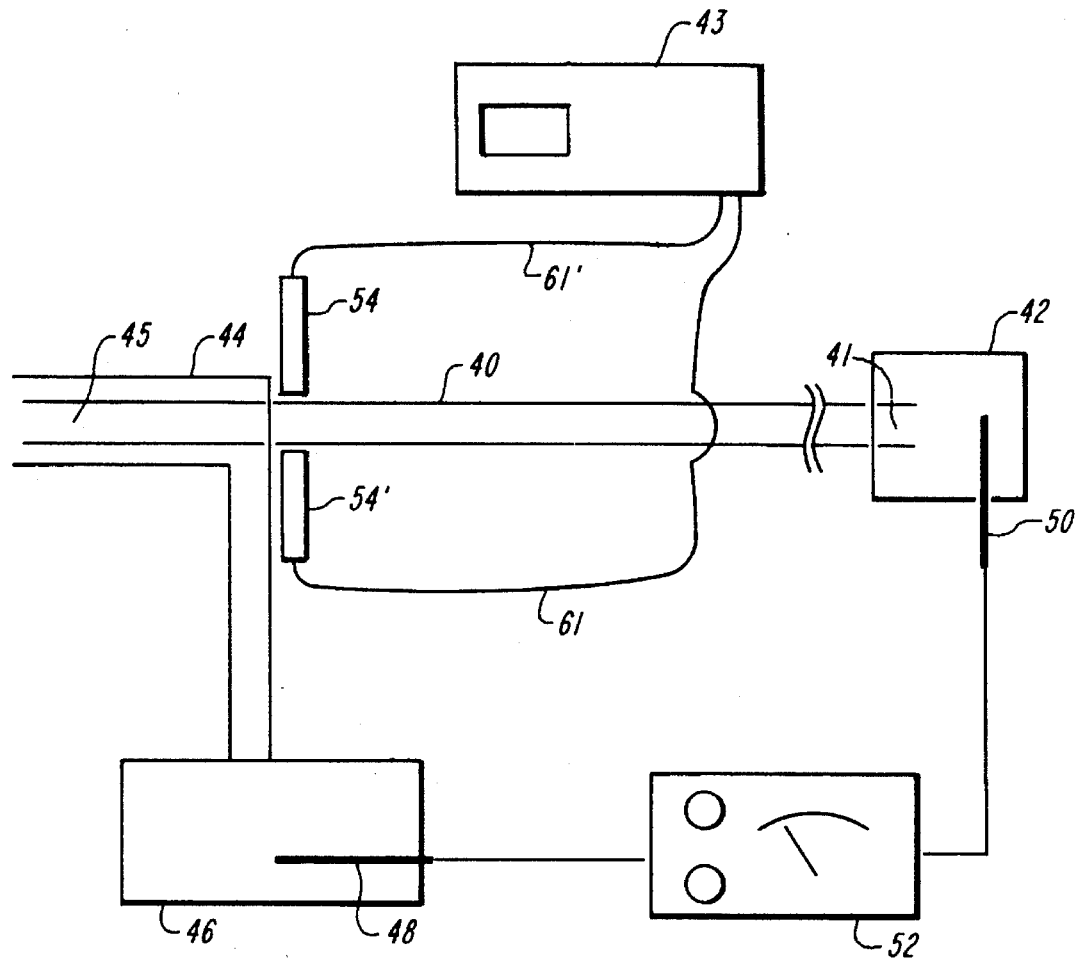
FIG. 1 is a schematic diagram of an embodiment of the capillary electrophoretic system of the invention.

The CE system and method of the invention have solved these problems of prior art systems. Referring to FIG. 1, a CE system of the invention includes, in general, a capillary 40, a detector 43 which may include optical fibers 61, 61', and a power supply 52. Capillary 40 is in contact at loading end 41 with a capillary electrophoresis buffer reservoir 42. The capillary electrophoresis buffer contained within reservoir 42 can be any buffer commonly used in capillary electrophoretic separations, such as a Tris-borate or a phosphate buffer. A sheath element 44 is attached over the exit end 45 of capillary 40 and permits a collection buffer from a collection buffer reservoir 46 to flow over the end of the capillary and transport materials as they emerge from the capillary tube. The collection buffer transfers the eluted molecules to analytical devices, such as a mass spectrometer for analysis by electrospray/mass spectroscopy, or to a collection vessel, such as a capillary, vial, or membrane. Capillary electrophoresis reservoir 42 and collection buffer reservoir 46 are in electrical contact through electrodes 48 and 50, respectively, and are connected to a high voltage power supply 52 to complete the required electrical circuit.

Figure 2:
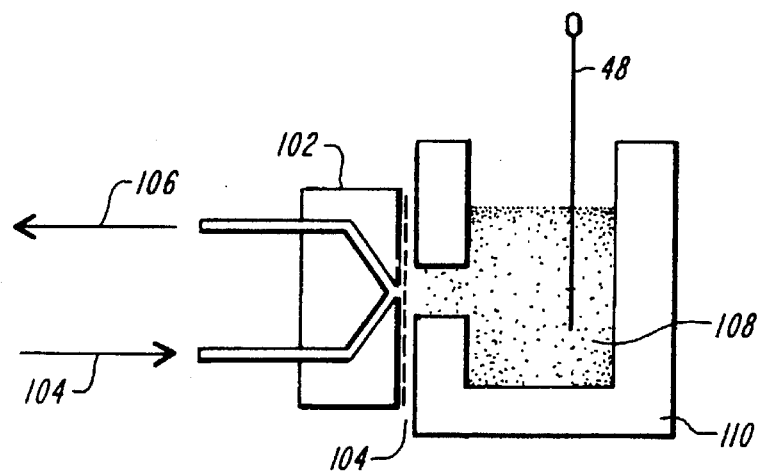
FIG. 2 shows a modification of the embodiment of FIG. 1.

When necessary, the electrode can be separated from the collection buffer by means of an ion permeable membrane. Referring to FIG. 2, in this configuration electrode 48 is immersed in electrolyte 108 in an electrode reservoir 110 and separated from the collection buffer by ion permeable membrane 104. Collection buffer flows through a flow-through block 102 via inlet port 104 and outlet port 106. Penetration of electrolysis product (which may cause changes in pH) would be eliminated. In this case the composition of the collection buffer may be different from the electrolyte used in the electrode reservoir. For example, a low ionic strength collection buffer can be used in this arrangement without the danger of penetration of the electrolysis products into the separation capillary.

The components of a sample are separated in the following manner. Samples of mixtures of charged molecules are loaded electrokinetically or by pressure at the loading end 41 of the capillary, and a high voltage is applied from high voltage power supply 52. The high voltage power supply 52 generates voltages corresponding to electric field strength of approximately 50–2000 volts/cm to force the charged molecules to migrate through capillary 40. As the mixture of charged molecules migrate through the capillary to its exit end 45, the molecules segregate according to their migration velocities into discrete zones, each zone containing a population of molecules with distinct electrophoretic properties. Optical fiber mounts 54, 54' position optical fibers 61, 61' at a distance of one cm or less from the outlet end of the capillary. As each zone passes the optical fibers, a signal is sent to detector 43, which registers and records the presence of the zone. Detection may be accomplished by methods known in the art, such as UV-Vis detection, fluorescence, or laser induced fluorescence.

The placement of optical fibers 61, 61' no more than a few cm from the outlet end 45 of the capillary, and more preferably no more than one cm from the end, is critical in the design of the invention. If optical fibers 61, 61' are positioned close to the outlet end 45 of capillary 40, precise correlation between detection of the zones and their emergence from the capillary can be achieved. At a distance of less than 1 cm, the uncertainty in the elution time is reduced to approximately 1 second. This reduction in error over the prior art enables precise and accurate collection of individual zones of any sample, e.g., DNA fragments, separated by CE. The close correlation between detection of a zone of material and its arrival at the end of the capillary allows the user to detect and collect the extremely small volumes eluting from the capillary and permits capillary electrophoresis to be used as a nanopreparative technique.

As individual zones of separated materials elute from capillary exit end 45, they are captured by the collection buffer, and the volume of the material in the zones is increased to a size that is more easily manipulated, e.g., 2–5 μl. The collection buffer may be used to transport the materials to analytical devices, such as a mass spectrometer for analysis by electrospray/mass spectroscopy, or to a collection vessel, such as a capillary, vial, or membrane.

Figure 3:
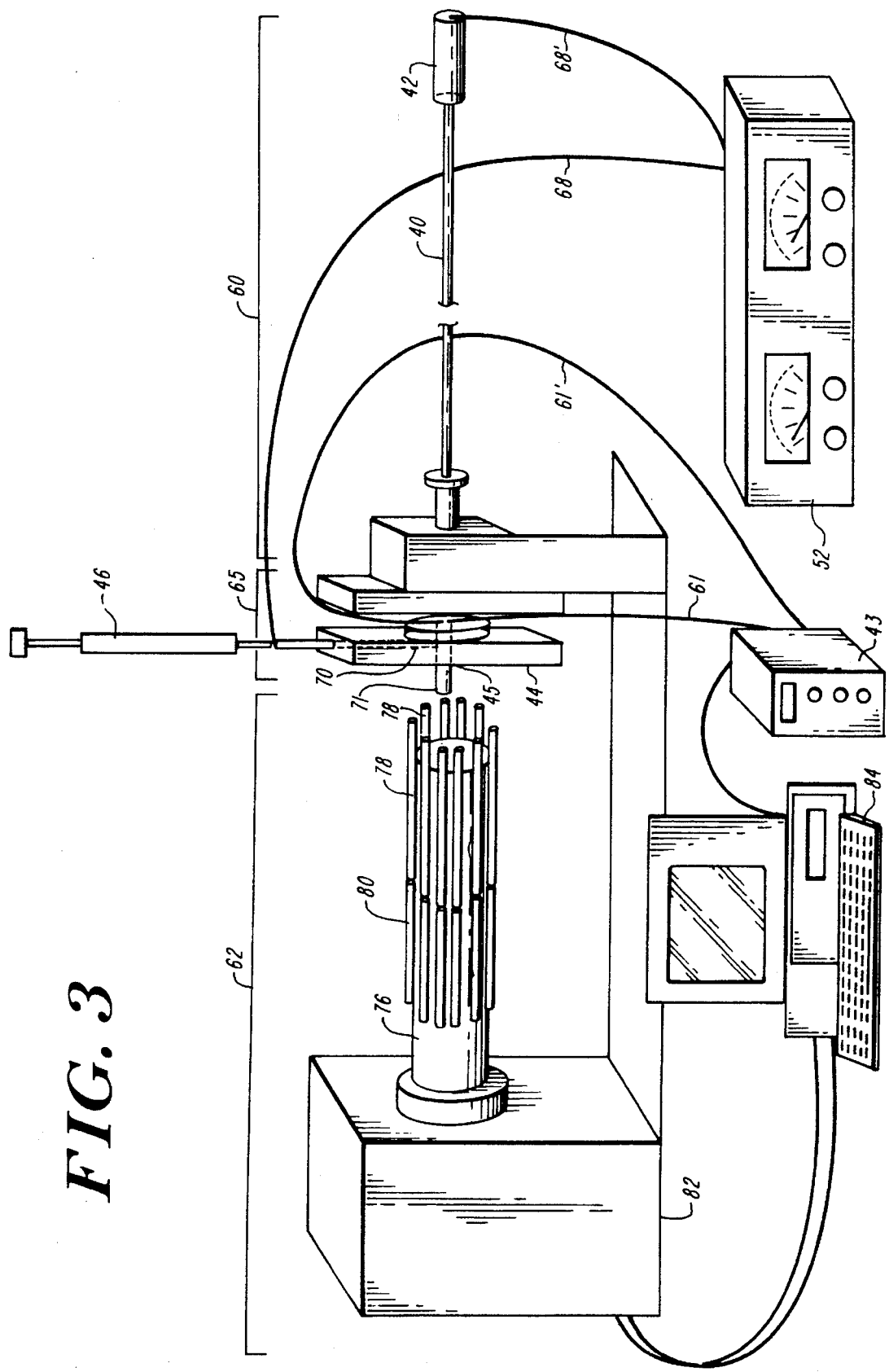
FIG. 3 shows the capillary electrophoretic system of the invention in combination with a collection apparatus.

Therefore, a fraction collection device may also be incorporated in the electrophoresis system described above to provide a method to collect the volumes of samples eluting from the capillary. Referring to FIG. 3, in this embodiment the complete system consists of three major components, a separation component 60, a detecting component 65, and a collection component 62. The separation component 60 includes the separation capillary 40 and buffer reservoir 42, which contains the capillary electrophoresis buffer. Capillary 40 may include a sieving matrix, such as linear polyacrylamide or the like, or an interaction matrix, such as polyvinylpyrollidone, to enhance separation effectiveness.

The detecting component 65 includes optical fibers 61, 61' and sheath 44 (for supplying collection buffer from a collection buffer reservoir 46) mounted over the exit end 45 of capillary 40. Capillary 40 is electrically connected via power lines 68, 68' to buffer reservoir 42 and sheath 44, thus forming the electrical circuit required for electric field generation. The ends of optical fibers 61, 61' are positioned approximately less than 1 cm from exit end 45 of the capillary, and the fibers are connected to a detector 43, which is in turn connected to a computer control station 84.

In this embodiment, the collection component 62 includes a rotor 76 on which a number of collection capillaries 78 are mounted by means of capillary holders 80. The collection capillaries 78 offer several advantages over conventional collection tubes. Materials collected into a capillary are less prone to evaporation due to the lower surface area in contact with the air. Collection capillaries take up less space than conventional tubes or vials and are better suited to collecting the small volumes that elute from a separation capillary.

During collection, a stepper motor 82 rotates the rotor 76 to bring the collection capillaries 78 into the correct position for collection of the eluant flowing from the end 71 of sheath 44. Stepper motor 82 is connected to the computer control station 84 to correlate detection of the materials by detector 43 with collection in the collection capillaries 78. With the configuration of the electrical circuit as described above, movement of the collection capillaries can be carried out without interrupting the electric field required for sample separation.

As a zone is detected by optical fibers 61, 61', detector 43 registers a signal, and after necessary calculations, computer 84 instructs stepper motor 82 to move a collection capillary 78 into position near the end 71 of the sheath. Collection buffer enters sheath 44 through the top of a "T" connection 70 and flows around the exit end 45 of the capillary 40. The collection buffer flows with a higher velocity than the migration velocity of the materials flowing through the capillary 40 and results in the separated molecules eluting in droplets from the end 71 of the sheath. Stepper motor 82 positions the end of the collection capillary extremely close to the end of the sheath (within a few hundred microns) so that capillary forces and surface tension can draw the eluting droplets into the collection capillary. In addition, a vacuum system can be used to transfer the droplets.

Figure 4:
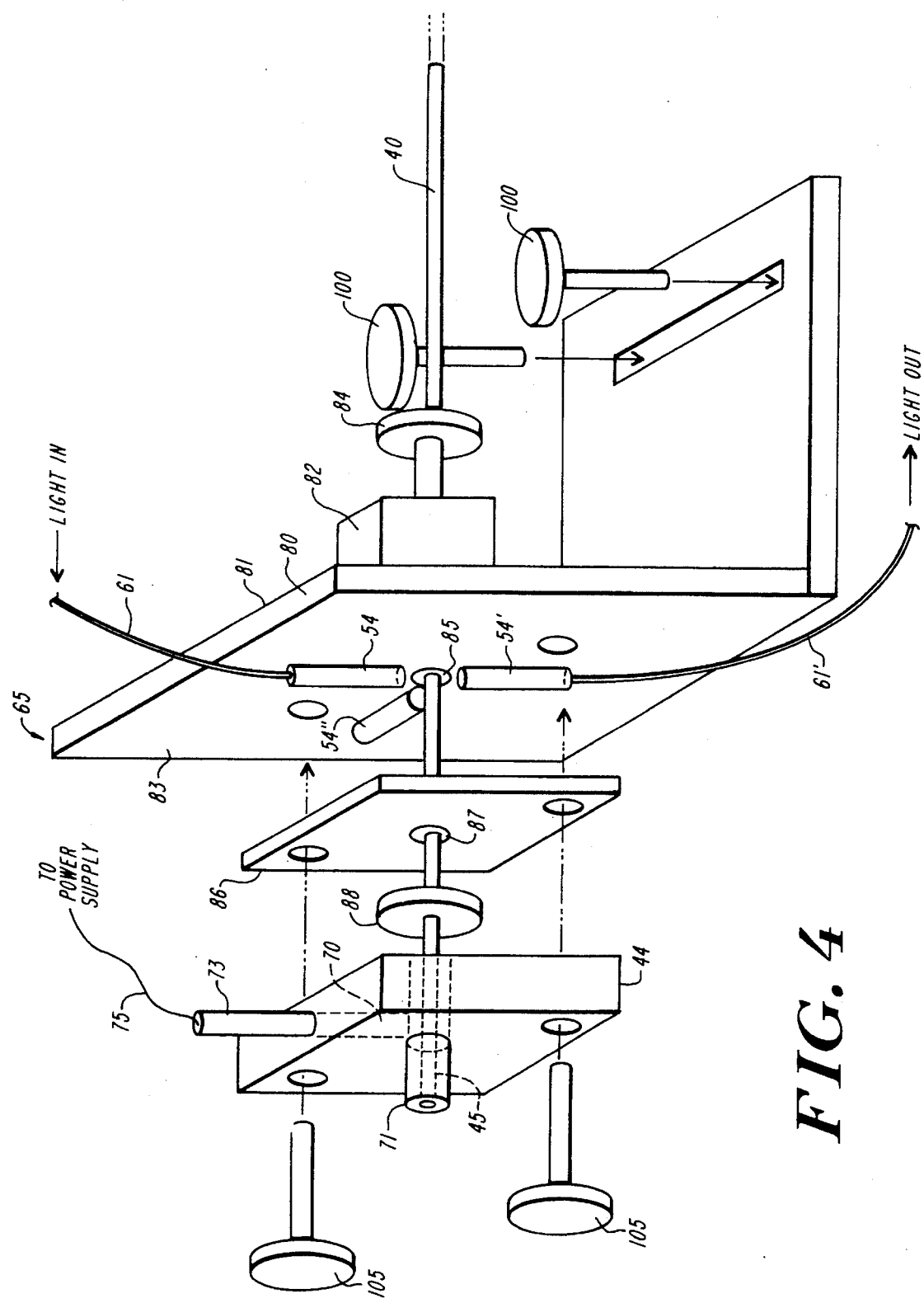
FIG. 4 is an exploded view of the detection and collection apparatus of a system of the invention.

FIG. 4 depicts the detecting and collecting component 65 in more detail. A mounting plate 80 includes a capillary guide block 82 and a septum 84 mounted on the plate outer face 81. Mounting plate 80 may be attached to a mounting surface by screws 100. Guide block 82 and Septum 84 guide capillary 40 through a hole 85 in the mounting plate. Optical fiber mounts 54, 54' and 54" are positioned in a "T"

arrangement on the inner face 83 of mounting plate 80 around a hole 85 to provide for a variety of detection capabilities. In one embodiment, optical fiber mounts 54 and 54' position optical fibers 61 and 61' on opposite sides of the capillary 40 for use with UV-Vis detectors. Light is provided by one optical fiber 61 and detected by the other optical fiber 61'. In another embodiment, optical fiber mounts 54 and 54" position the optical fibers perpendicularly around hole 85. This arrangement is required for use with fluorescence spectroscopy detection or laser induced fluorescence to prevent detection interference with the incident light.

A spacer plate 86 is mounted adjacent to the optical fiber mounts 54, 54', 54". Capillary 40 passes through a hole 87 in a spacer plate 86, and the end of the capillary is positioned in the sheath 44. Sheath 44 includes a "T" connection 70 consisting of branch 71 extending through the sheath which accepts the exit end of the capillary, and branch 73 extending to the top of the sheath which provides an access port for collection buffer and allows the collection buffer to flow over the end of the capillary. An electrical connection 75 is made with sheath 44 at the tope of "T" branch 73. The collection buffer thus completes the electrical circuit with the exit end 45 of the capillary and causes the molecules of the sample to migrate through the capillary. However, the electrical connection itself is decoupled from the exit end 45 of the capillary to prevent electrical damage to the samples as they elute from the capillary. A septum 88 is positioned between spacer plate 86 and sheath 44 to prevent collection buffer from flowing back along the outside of the capillary 40. Sheath 44 and spacer plate 86 are attached to mounting plate 80 by screws 105.

EXAMPLE

Figure 5:
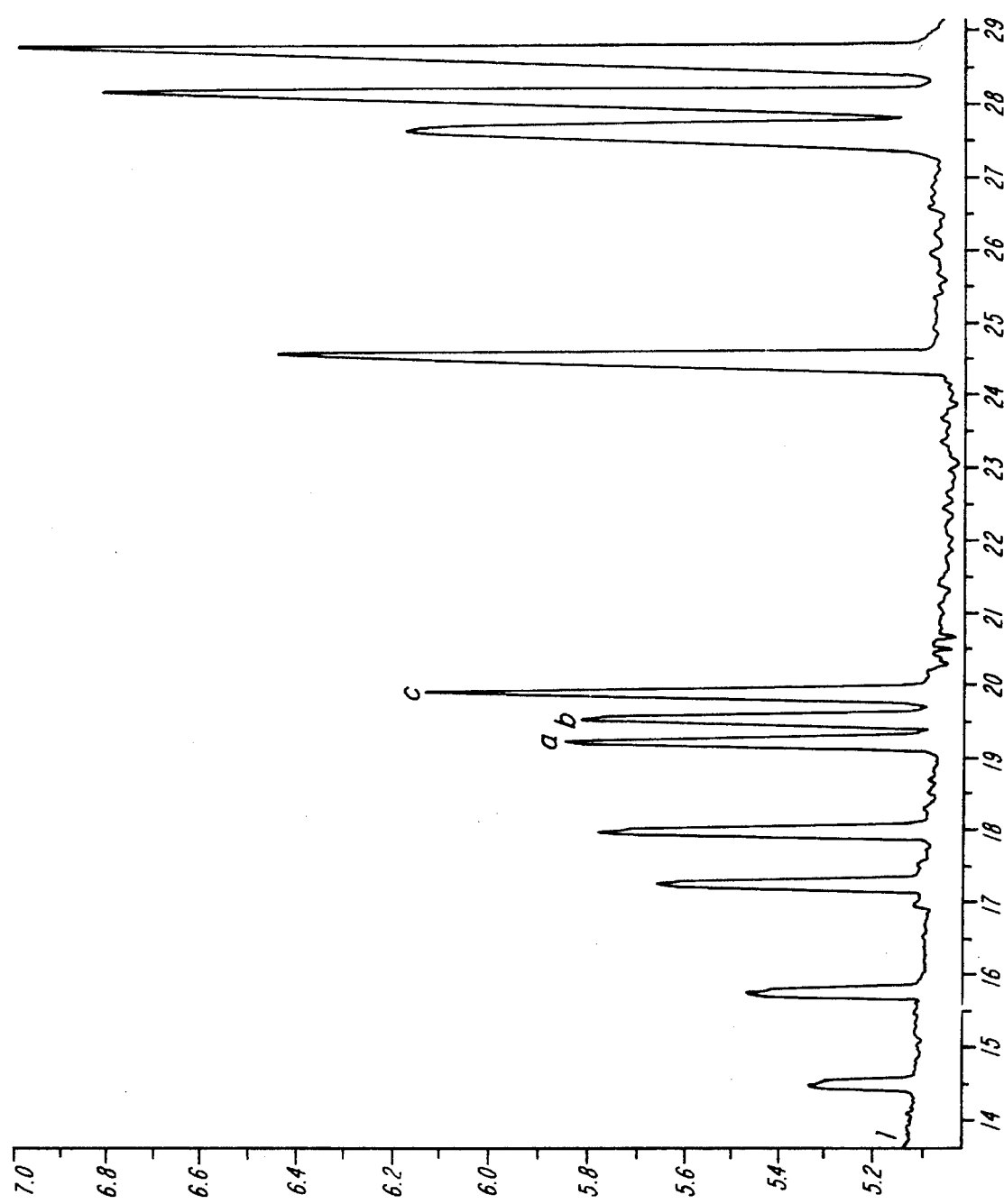
FIG. 5 is a capillary electropherogram of a Hae III digest of ΦX174 DNA.

The invention can be utilized to analyze the restriction digest pattern of DNA digested with restriction enzymes. FIG. 5 shows the capillary electropherogram of commercially available Hae III digest of ΦX174 DNA. A 100 μm capillary (total length 25 cm; effective length 24.1 cm) coated with linear polyacrylamide was filled with a solution of 5% linear polyacrylamide (LPA) in Tris-borate-EDTA buffer. A sample of the Hae III digest was loaded electrokinetically into the capillary and subjected to an electric field of approximately 160 V/cm (13 μA). The elution time of each fragment was automatically calculated according to the average velocity measured at the detection window. The closely spaced peaks, the triplet a, b, and c, were successfully collected in separate fractions using the method of the invention.

Figure 6A:
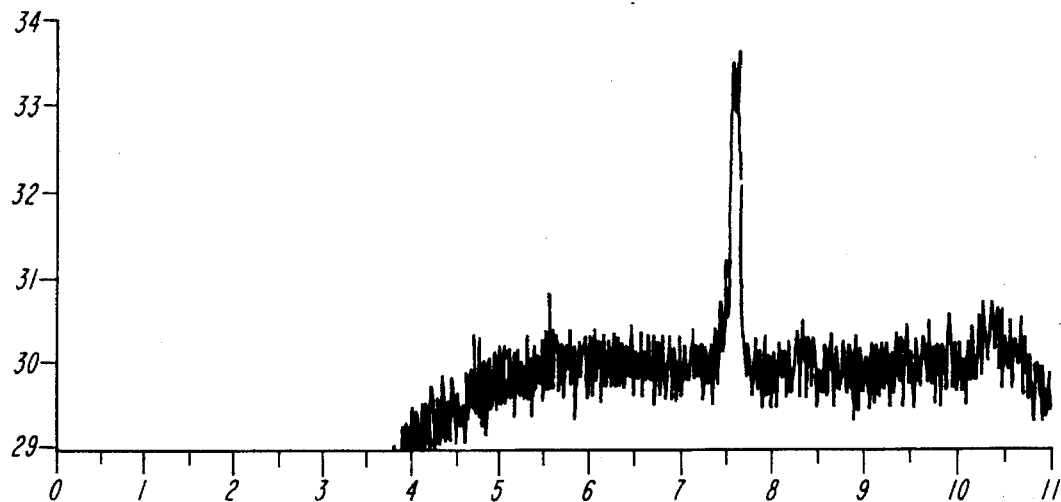
FIG. 6A is a capillary electropherogram of the 281 base pair fragment isolated as shown in FIG. 5.
Figure 6B:
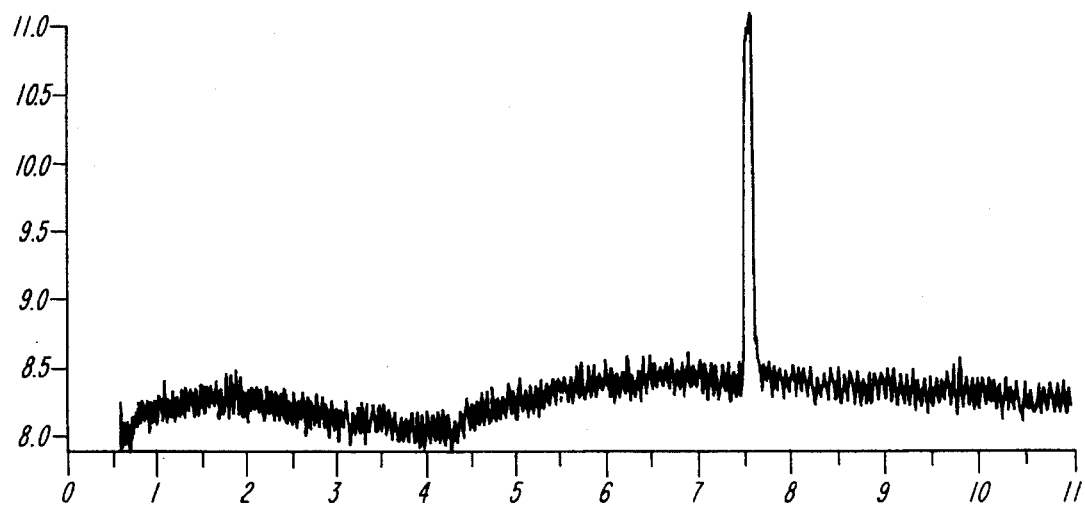
FIG. 6B is a capillary electropherogram of the 271 base pair fragment isolated as shown in FIG. 5.
Figure 6C:
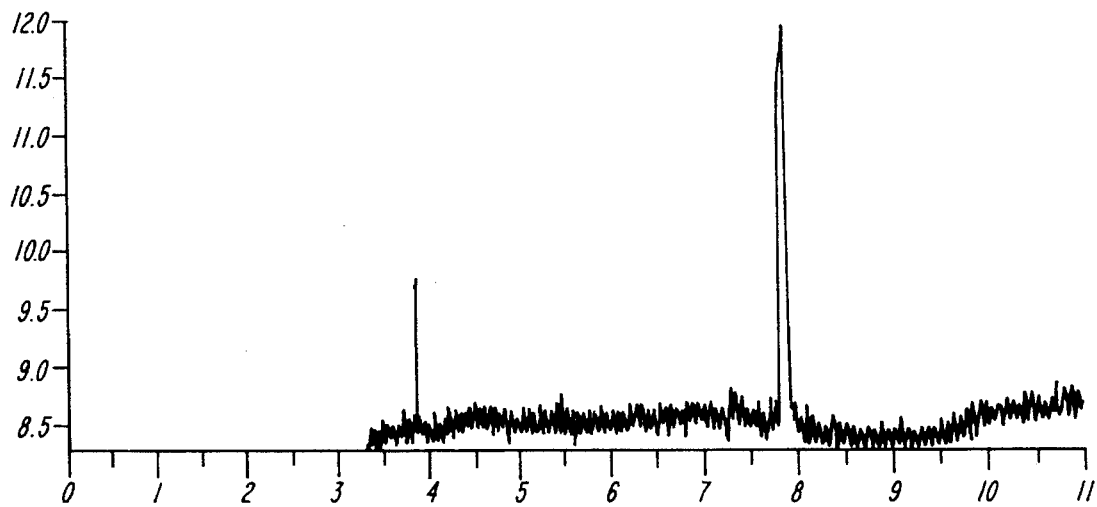
FIG. 6C is a capillary electropherogram of the 310 base pair fragment isolated as shown in FIG. 5.

FIGS. 6A, 6B, and 6C show purity profiles following analysis of fractions corresponding to peaks a, b, and c, respectively, as collected in FIG. 5. It can be seen that the fragments corresponding to the individual peaks are essentially free of contaminating DNA molecules. Unexpectedly, following PCR amplification with appropriate primers and laser induced fluorescence analysis of the collected fractions (using the intercalator ethidium bromide), determination of fragment length revealed that the elution order of the DNA fragments was 281 bp, 271 bp and 310 bp.

During electrophoretic separation of DNA in a sieving matrix, individual DNA fragments are generally separated according to their length or base pair number. The identity (i.e., length of fragment) of peaks a, b, and c from a Hae III digest of ΦX174 DNA was uncertain in previous literature reports and was presumed to be 271 bp, 281 bp and 310 bp. However, using the method of the invention, each fragment was isolated and correctly identified. These results further indicate that the invention is a powerful method to isolate and collect fractions eluting from a capillary electrophoresis column, and that the fractions collected are essentially pure and ready for subsequent analytical steps.

Other embodiments of the invention are also useful for detecting and collecting molecules eluting from the capillary. For example, a sheath for collection buffer and a detector, most preferably including optical fibers, may be positioned at the interface between the exit end of the separation capillary and a collection capillary. In this configuration, the interface distance is approximately 150 μm and is contained within the sheath. Collection buffer flows around the interface and allows eluted materials to be collected in the collection capillary. In an alternative embodiment, detection may be performed after elution from the capillary. As the molecules elute from the end of the capillary, collection buffer directed by the sheath passes over the end of the capillary and collects the eluted materials. Optical fibers are positioned after the end of the capillary to detect the exiting molecules, after their elution.

Although the invention has been shown and described with respect to illustrative embodiments thereof, it should be appreciated that the foregoing and various other changes, omissions and additions in the form and detail thereof may be made without departing from the spirit and scope of the invention as delineated in the following claims.

We claim:

1. A capillary electrophoretic system comprising:
   a separation capillary having an inlet end and an outlet end, said capillary having the capacity to separate a sample of molecules traversing said capillary from said inlet end to said outlet end in an electric field;
   an electrophoresis buffer reservoir positioned to provide electrophoresis buffer at said inlet end of said capillary;
   a detector positioned less than ten centimeters from said outlet end of said capillary, said detector having the capacity to detect said separated molecules, without post-separation processing of said separated molecules prior to detection; and
   a sheath surrounding said outlet end of said capillary, said sheath positioned to permit a collection buffer to flow over said outlet end and mix with separated molecules from said sample as said separated molecules exit from said outlet end, wherein said capillary, said electrophoresis buffer reservoir and said collection buffer in said sheath are in electrical contact in an electrical circuit, said circuit having the capacity to provide said electric field.

2. The capillary electrophoretic system of claim 1, further comprising a collection vessel adjacent to said outlet end of said separation capillary to collect said separated molecules.

3. The capillary electrophoretic system of claim 2, wherein said collection vessel comprises at least one vial membrane.

4. The capillary electrophoretic system of claim 2, wherein said collection vessel comprises at least one collection capillary.

5. The capillary electrophoretic system of claim 4, wherein said collection capillary is positioned adjacent to said outlet end of said separation capillary by a stepper motor.

6. The capillary electrophoretic system of claim 4, wherein said collection capillary is positioned within several hundred microns of said outlet end of said separation capillary.

7. The capillary electrophoretic system of claim 1, further comprising an analytical device adjacent to said outlet end of said separation capillary.

8. The capillary electrophoretic system of claim 7, wherein said analytical device comprises a mass spectrometer.

9. The capillary electrophoretic system of any one of claims 1, 2 or 7, wherein said detector and said electrical circuit are in communication for providing feedback from said detector to control said electric field provided by said circuit.

10. The capillary electrophoretic system of claim 1, wherein said detector is positioned less than one centimeter from said outlet end of said capillary.

11. The capillary electrophoretic system of claim 1, wherein said detector comprises a UV-Vis detector.

12. The capillary electrophoretic system of claim 1, wherein said detector comprises a fluorescence detector.

13. The capillary electrophoretic system of claim 1, wherein said detector comprises optical fibers.

14. The capillary electrophoretic system of claim 1, wherein said capillary comprises a sieving matrix or an interaction matrix.

15. The capillary electrophoretic system of claim 1, wherein said separation capillary comprises an open tube for capillary zone electrophoresis (CZE), with or without electroosmotic flow.

16. The capillary electrophoretic system of claim 1, wherein said detector is positioned before said outlet end of said capillary.

17. The capillary electrophoretic system of claim 1, wherein said detector is positioned after said outlet end of said capillary.

18. The capillary electrophoretic system of claim 1, wherein said collection buffer and an electrode for providing said electrical contact are separated by an ion permeable membrane.

19. A method of separating a sample of molecules comprising:
providing a capillary electrophoretic system, said system comprising,
a separation capillary having an inlet end and an outlet end,
an electrophoresis buffer reservoir positioned to provide electrophoresis buffer at said inlet end of said capillary,
a detector positioned less than ten centimeters from said outlet end of said capillary, and
a sheath surrounding said outlet end of said capillary and positioned to permit a collection buffer to flow over said outlet end of said capillary;
providing a sample of molecules;
loading said sample of molecules into said inlet end of said capillary;
establishing an electrical circuit comprising said capillary, said electrophoresis buffer reservoir and said collection buffer in said sheath;
activating said electrical circuit to provide an electric field along said capillary;
separating said sample of molecules in said capillary in said electric field;
detecting said separated molecules with said detector, without post-separation processing of said separated molecules prior to said detecting; and
permitting said collection buffer in said sheath to flow over said outlet end of said capillary, said collection buffer mixing with separated molecules from said sample as said separated molecules exit from said outlet end of said capillary.

20. The method of claim 19, wherein in said step of providing a capillary electrophoretic system said detector in said system is positioned less than one centimeter from said outlet end of said capillary.

21. The method of claim 19, wherein in said step of providing a capillary electrophoretic system said detector comprises optical fibers.

22. The method of claim 19, further comprising the step of collecting said mixture of collection buffer and molecules.

23. The method of claim 22, wherein said collecting step includes collecting said mixture in at least one vial or on at least one membrane.

24. The method of claim 22, wherein said collecting step includes collecting said mixture in at least one collection capillary.

25. The method of claim 19, further comprising the step of analyzing said mixture of sheath fluid and molecules.

26. The method of claim 25, wherein said analyzing step includes mass spectroscopy.

27. The method of claim 25, wherein said analyzing step includes electrospray mass spectroscopy.

28. The method of claim 19, wherein said detecting step includes UV-Vis detection.

29. The method of claim 19, wherein said detecting step includes fluorescence detection.

30. The method of claim 19, wherein said separation capillary includes a sieving matrix or an interaction matrix.

31. The method of claim 19, wherein said separation capillary comprises an open tube for capillary zone electrophoresis (CZE), with or without electroosmotic flow.

32. The method of claim 19, wherein said separating step comprises isoelectric focusing.

33. The method of claim 19, wherein said detector and said electrical circuit are in communication and said detecting step further includes providing feedback from said detector to control said electric field provided by said circuit.

34. A capillary electrophoretic system comprising:
a separation capillary having an inlet end and an outlet end, said separation capillary having the capacity to separate a sample of molecules traversing said separation capillary from said inlet end to said outlet end in an electric field;
an electrophoresis buffer reservoir positioned to provide electrophoresis buffer at said inlet end of said separation capillary;
a detector positioned less than one centimeter before said outlet end of said separation capillary, said detector having the capacity to detect said separated molecules, without post-separation processing of said separated molecules prior to detection;
a sheath surrounding said outlet end of said separation capillary, said sheath positioned no permit a collection buffer to flow over said outlet end and mix with separated molecules from said sample as said separated molecules exit from said outlet end; and
a collection vessel comprising at least one collection capillary adjacent to said outlet end of said separation capillary to collect said separated molecules, wherein said separation capillary, said electrophoresis buffer reservoir and said collection buffer in said sheath are in electrical contact in an electrical circuit, said circuit having the capacity to provide said electric field.

35. The capillary electrophoretic system of claim 34, wherein said collection capillary is positioned adjacent to said outlet end of said separation capillary by a stepper motor.

36. The capillary electrophoretic system of claim 5 or claim 35, wherein feedback is provided from said detector to control said stepper motor.

37. The capillary electrophoretic system of claim 34, wherein said collection capillary is positioned within several hundred microns of said outlet end of said separation capillary.

38. The capillary electrophoretic system of claim 34, wherein said detector and said electrical circuit are in communication for providing feedback from said detector to control said electric field provided by said circuit.

39. A capillary electrophoretic system comprising:

a separation capillary having an inlet end and an outlet end, said separation capillary having the capacity to separate a sample of molecules traversing said separation capillary from said inlet end to said outlet end in an electric field;

an electrophoresis buffer reservoir positioned to provide electrophoresis buffer at said inlet end of said separation capillary;

a detector positioned less than one centimeter before said outlet end of said separation capillary, said detector having the capacity to detect said separated molecules, without post-separation processing of said separated molecules prior to detection;

a sheath surrounding said outlet end of said separation capillary, said sheath positioned to permit a collection buffer to flow over said outlet end and mix with separated molecules from said sample as said separated molecules exit from said outlet end; and a mass spectrometer adjacent to said outlet end of said separation capillary to receive said separated molecules for analysis, wherein said separation capillary, said electrophoresis buffer reservoir and said collection buffer in said sheath are in electrical contact in an electrical circuit, said circuit having the capacity to provide said electric field.

\* \* \* \* \*